United States Patent [19]

Cheung et al.

[11] Patent Number: 5,603,835
[45] Date of Patent: Feb. 18, 1997

[54] TRIMETHYLOLPROPANE COLOR IMPROVEMENT

[75] Inventors: Hung-Cheun Cheung; Rodolfo W. Laurel; George C. Seaman, all of Corpus Christi, Tex.

[73] Assignee: Hoechst Celanese Corporation, Somerville, N.J.

[21] Appl. No.: 278,352

[22] Filed: Jul. 21, 1994

Related U.S. Application Data

[63] Continuation-in-part of Ser. No. 184,797, Jan. 19, 1994, abandoned.

[51] Int. Cl.$^6$ ................................................. B01D 11/04
[52] U.S. Cl. ........................... 210/639; 210/634; 210/192
[58] Field of Search ............................... 210/634, 638, 210/511, 192, 639; 568/853, 854

[56] References Cited

U.S. PATENT DOCUMENTS 3,956,406   5/1976   Palmer et al. ..................... 260/637 P

*Primary Examiner*—Frank Spear
*Attorney, Agent, or Firm*—Donald R. Cassady; M. Susan Spiering

[57] ABSTRACT

This invention relates to a process for improving the color of trimethylolpropane (TMP) by extracting color-causing impurities generated in the reaction to produce TMP. This improved color TMP is characterized by a reduced acid wash color and phthalic anhydride color—color measurement tests commonly used in the industry for assessing product quality and suitability of the TMP for certain color sensitive end-uses.

14 Claims, No Drawings

TRIMETHYLOLPROPANE COLOR IMPROVEMENT

RELATIONSHIP TO PRIOR APPLICATIONS

This application is a continuation-in-part of application Ser. No. 08/184,797, filed Jan. 19, 1994, now abandoned.

BACKGROUND OF THE INVENTION

This invention relates to a process for improving the color of trimethylolpropane (TMP) by extracting color-causing impurities generated in the reaction to produce TMP. This improved color TMP is characterized by a reduced acid wash color and phthalic anhydride color—color measurement tests commonly used in the industry for assessing product quality and suitability for certain color sensitive end-uses. This acid wash color and phthalic anhydride color are collectively referred to as reacted color.

Trimethylolpropane is produced by the reaction of n-butyraldehyde and formaldehyde in the presence of a strong base, such as sodium hydroxide. A formate salt is produced as a co-product (sodium formate if sodium hydroxide is used) with the TMP. After neutralization of the excess base, the TMP is recovered from the aqueous solution containing the formate salt and neutralized base generally by solvent extraction, e.g. using solvents such as ethyl acetate, isobutanol, butyl acetate, and the like. The TMP is then separated from the organic solvent phase, for example by distillation. Another method for the removal of the TMP from the initial reaction mixture, separating the TMP from the formate salt and neutralized base aqueous solution, is to use two solvents, one solvent in which the TMP is very soluble, e.g. isobutanol, and a second solvent, in which the formate salt and neutralized base are insoluble, in an amount sufficient to separate the aqueous phase from the first solvent, but not sufficient to separate out the TMP. The organic phase with the extracted TMP and other organic compounds is separated from the aqueous phase by decantation and the first solvent removed by distillation. Typically the second solvent is a non-polar solvent, e.g.: xylene, with a boiling point greater than the first solvent. The TMP/second organic solvent mixture is allowed to settle and cool and the separated TMP is removed by decantation. An example of this separation is published as U.S. Pat. No. 3,956,406 to Palmer et al. The recovered crude TMP is then purified by conventional distillation under vacuum to yield a finished TMP product. These processes generally produce a TMP product which has an acid-wash color of about 5–10 Gardner units or phthalic anhydride color of about 100–300 APHA units. Other TMP processes have produced product having an acid-wash color of about 5–6 Gardner units. However, for many applications, e.g. in producing TMP acrylate esters for radiation-cured coatings, it is desirable to obtain product having an acid-wash color of 3 or less Gardner units and phthalic anhydride color of less than 100 APHA units.

SUMMARY OF THE INVENTION

Thus, it is an object of this invention to provide an efficient process for the production of TMP having an acid-wash color in the range of from about 0 to about 3 Gardner units and phthalic anhydride color in the range of from about 0 to about 100 APHA units.

In accordance with this invention there is provided a process for obtaining TMP having an acid-wash color in the range of from about 0 to about 3 Gardner units and a phthalic anhydride color of less than 100 APHA units. The process comprises contacting an aqueous solution of the TMP which has previously been recovered from the initial reaction mixture, as described above with an organic solvent for removing the color bodies, in which TMP is only partially soluble, and obtaining in greater than about 60% yield reduced color TMP product from the aqueous phase having an acid-wash color of 3 or less Gardner units. The phthalic anhydride color of the TMP product is less than 100 APHA units.

In accordance with one aspect of this invention, the separation of color bodies from finished purified TMP, that is TMP that has been recovered after typical commercial purification and distillation as previously described, is carried out by either batch or continuous liquid-liquid extraction.

In accordance with another aspect of this invention, the separation of color bodies from crude TMP is carried out by either batch or continuous liquid-liquid extraction. By crude TMP is meant that TMP which has been separated from the initial reaction mixture of formate salt and neutralized base in water solution but not further purified, e.g. before drying or distillation.

More particularly, the present invention adds an extraction step to the known process for purifying TMP. The extraction can be carried out on either crude or finished TMP product using either fresh or recycled solvent. The extraction requires the feed to be an aqueous solution of TMP. Accordingly, water may be added to the TMP feed as needed.

Although either batch or continuous extraction may be used in the invention advantageously, the process is preferably carried out using a continuous extraction with recycle streams.

Thus, according to the present invention the TMP is dissolved in water and contacted with a partially or sparingly water—TMP miscible solvent. The color bodies are removed from the water/TMP solution by the solvent, typically by liquid/liquid extraction, while, at the same time, extracting little of the TMP from the aqueous phase into the solvent phase, thus insuring a high recovery of reduced color TMP product from the aqueous phase. The added water is removed from the TMP by processes well known in the art.

Preferentially ethers, such as, for example, ethyl tert. butyl ether, diethyl ether, dipropyl ether, methyl tert. butyl ether, or diglyme, and esters, such as, for example, esters containing from 2 to about 9 carbon atoms, i.e.: methyl formate, methyl acetate ethyl formate, ethyl acetate, butyl propionate, and the like, and esters of ethylene glycol, propylene glycol, or the like with $C_1$–$C_4$ acids or mixtures of the aforementioned solvents are used in the extraction.

Both reacted color and the amount of TMP recovered by the process of the instant invention (TMP recovery efficiency) are influenced by the same variables. These variables include temperature, feed water content, amount of solvent, contact time, and number of extraction stages. For example, reacted color and recovery efficiency increase as feed composition of TMP, in weight percent, increases and as the solvent to feed weight ratio increases. Therefore, these variables are optimized to achieve the desired reacted color and TMP recovery efficiency.

The pressure used to carry out the process is not critical and the process can advantageously be carried out at atmospheric pressure, sub-atmospheric, or elevated pressure, preferably at atmospheric pressure.

The unrecovered TMP can be recycled back through the process or disposed of by known methods, although it is clear that an initial high TMP recovery is desirable to reduce operating costs.

A continuous, countercurrent, once-through extraction of the process of the instant invention can be carried out at from about 0° C. to about 100° C., preferably from about 15° C. to about 40° C., using the solvent as the disperse phase or as the continuous phase, a solvent to feed weight ratio of from about 5:1 to about 1:2 preferably about 4:1 to 2:1, and a feed of from about 30% to about 80% TMP in water, preferably from about 45% to about 65%.

The process is typically carried out using extraction equipment known in the art. For example, a York-Scheibel® extractor or a sieve plate extractor can be used to demonstrate the advantages for the instant claimed process.

The acid wash color of the TMP is determined using a sulfuric acid wash color test. In the test molten TMP is extracted with toluene, followed by washing the extract with sulfuric acid. The reacted color is monitored through a colorimeter in Gardner units.

a. Reference standards for color tests.

In performing color tests, a Hunter Lab Tristimulus Colorimeter (ColorQuest #C4188) and software (#CMR-884) is used. ASTM color standards are used for calibration according to ASTM Method D 1544-80.

b. Cell Sizes

Color is shown to be dependent on cell sizes. Therefore a cell of 10-mm pathlength is used for all color analysis.

c. Shaking

Color depends on the intensity of shaking the toluene extract with acid. Vigorous shaking is needed to ensure sufficient mixing between phases.

STANDARD ACID WASH COLOR TEST

1. Add 20 g of TMP (to 0.1 g accuracy, crystalline or molten) to a 200 ml tared beaker. Add 80 g of reagent grade toluene (acid wash color of about 1 Gardner unit).
2. Heat the solution with rapid agitation to 60° C. for 5 minutes. Use a magnetic stirring bar. Start timing at 60° C. once all the TMP melts.
3. Charge 75 ml (+/−1 ml) of the upper toluene phase to a 250 ml separatory funnel (decant or pipette). Add 25 ml (+/−1 ml) of concentrated sulfuric acid to the separatory funnel using a graduated cylinder. Shake the separatory funnel vigorously for 30 seconds, being sure that different phases mix thoroughly. Allow 4 minutes for the solution to phase out. The solution should show a temperature of about 45 +/−2° C. Decant the acid phase (bottom layer).
4. Add a sufficient amount of the acid-phase to a 10-mm *Gardner cuvette. Record color by means of a Hunter Lab Tristimulus Colorimeter. Data are noted to the nearest number in Gardner units by using a special program, ColorQuest #C4188. This software converts chromaticity coordinates from the spectral transmittance data to Gardner units. The colorimeter is calibrated by using ASTM color standards (e.g. $K_2PtCl_6$) and color-disks.

* A Gardner tube and a comparator can be used to replace the colorimeter.

The phthalic anhydride color test is determined by reacting TMP with phthalic anhydride at elevated temperature. The resultant polymer develops a color which is measured using a colorimeter in APHA units.

PHTHALIC ANHYDRIDE COLOR TEST

Apparatus:

1. Bausch and Lomb Spectronic 20 (Spec 20).
2. Cuvettes for the Spec 20.
3. Wax or paraffin bath—A stirred, constant temperature wax bath capable of maintaining a temperature of 200 +/−5.0° C.
4. Platinum-Cobalt color standards (dilute from 1500 Pt-Co Standard).
5. Vortex mixer.
6. Timer.

Reagents:

1. Aldrich Brand Phthalic Anhydride (99%). (note: brand of phthalic anhydride can affect final color.)

Procedure:

1. Place a 2.00 gram sample in a cuvette and add 2.00 grams of the phthalic anhydride reagent. Cork the cuvette.
2. Suspend the cuvette in a wax bath maintained at 200 +/−2° C. Set the timer for 30 minutes. Allow the cuvette to remain in the wax bath until the solution melts and becomes clear (approximately 10 minutes), then remove the sample from the bath and wipe off the excess wax. Immediately place the cuvette on the vortex stirrer and allow to stir for 20 seconds or until the sample is thoroughly mixed. Repeat the procedure for all samples.
3. After mixing, suspend the cuvette in the wax bath until the 30 minute reaction time is completed. At the end of the reaction time remove the samples and wipe off the excess wax.
4. Allow the samples to cool to room temperature for 30 minutes.
5. Calibrate the Spec 20 instrument during the cool down time. Set the wavelength dial to 460 nm. Adjust to full scale (0 abs) with water as the blank. Then read the absorbance of the 375, 750, and 1125 Pt-Co color standards. Prepare an absorbance versus Pt-Co color graph from the results of these readings.
6. Read the color absorbance of the sample cuvettes at 460 nm on the Spec 20.
7. Determine the Pt-Co color of the samples by matching the absorbance of the sample with the corresponding color reading based upon the standard curve. Record the results as Pt-Co color units.

The correspondence of Gardner units to APHA units is shown in Table I.

TABLE I

| Acid Wash Test Gardner units | Phthalic Anhydride Test APHA units |
| --- | --- |
| 0–1 | 0–40 |
| 4–5 | 70–100 |
| 6–7 | 170–200 |
| 8–10 | 200–300 |

The following non-limiting examples are provided to illustrate this invention further. All proportions are by weight unless otherwise indicated.

EXAMPLE 1

The reacted color of purified TMP was significantly reduced by the following process. A perforated plate-column extractor used in this example was a 1-inch inside diameter jacketed column with beaded joints at both ends, having 10 trays per section, thermal well between the fifth and sixth trays. The column contained 30 sieve trays. To reduce flooding tendencies and to improve control of the interface level between the organic solvent and aqueous phases, a large (4 inch inside diameter×18 inch long) phase separator was used at the top of the column.

The counter-current liquid-liquid extraction was carried out at 35° C. using methyl tert. butyl ether (MTBE) as the solvent and it was the continuous phase in the extraction. A 2.5:1 MTBE: aqueous feed ratio by weight was used with a feed composition of 60% TMP in water added at a rate of 15 grams per minute. The extraction was continued for 12 hours. The average recovery of improved color TMP was 89% by weight based on starting TMP and had an average acid wash color of 0.7 Gardner units and an average phthalic anhydride color of 30 APHA units. This compared to an average acid wash color of 9–10 Gardner units and an average phthalic anhydride color of 2–300 APHA units for the starting TMP material.

In the next example, the effect of recovery and recycle of the organic solvent used for extracting the color bodies and the water from the TMP aqueous feed simulating a complete, continuous commercial process, is illustrated. Again the reacted color is significantly reduced for the recovered TMP product compared to the starting TMP.

EXAMPLE 2

Using the perforated plate extractor as described in Example 1, the counter-current, liquid-liquid extraction was carried out at 35° C., using MTBE as solvent and the continuous phase. The MTBE feed rate was 30 g/minute and the aqueous feed containing 60% TMP, was added at a rate of 12.5 g/minute.

For the first 8 hours, pure TMP, fresh MTBE and water were used to establish steady-state conditions in the extractor. After 8 hours and for the next 28 hours, the MTBE solvent and water used to dissolve the TMP were recovered and recycled. The extract from the extractor was flashed in a MTBE flasher at about 55° C. The MTBE flasher consisted of a 10-tray 1 inch inside diameter Oldershaw column with a reboiler at the base. The recovered overhead MTBE from the flasher was recycled for extraction. About 10% of the flasher residue was used for TMP recycle.

The raffinate from the extractor was flashed in a reboiler at 125° C. The overhead of flashed water was recovered and recycled as the water to make up the aqueous TMP feed to the extractor column. The residue after removing the water consisted of reduced reacted color TMP containing less than 10% water. The progress of the extraction was monitored by testing the color of this residue every 6 hours.

The average recovery of improved color TMP was 92% by weight. The resulting product had an average acid wash color of 0.7 Gardner units and an average phthalic anhydride color of 30 APHA units.

At the 36th hour a small amount of TMP of high reacted color (color 8.4 Gardner units) was added to imitate TMP recycle. The feed was composed of MTBE flasher residue (color 16 GU) and pure TMP (color 8 GU). The extraction results remained comparable to earlier in the run.

No build up of color in the recovered TMP product is evident, even with continuous recovery and recycle of the extracting solvent and the makeup water for the aqueous TMP feed. Color bodies contributing to the reacted color of the TMP have been markedly reduced and removed by the process, while, at the same time, maintaining a high recovery efficiency of TMP product.

The results are set forth in Table II.

TABLE II

| Time (hours) | Acid Wash Color of the Recovered TMP (Gardner Units) |
| --- | --- |
| 6 | 0.6 |
| 12 | 0.6 |
| 18 | 0.6 |
| 24 | 0.7 |
| 30 | 0.5 |
| 36 | 0.6 |
| 42 | 0.6 |
| 48 | 0.7 |
| 51 | 0.7 |

The following example illustrates the process of the instant invention operated in a batch mode instead of a continuous mode of operation. It is clear that more or less extraction stages can be used depending on the degree of reacted color reduction desired and the desired recovery efficiency of the final TMP product. There will of course be an optimal number of stages based on the particular economics of the operation, since each extraction step adds to the cost of the operation while at the same time reducing reacted color with each step.

EXAMPLE 3

1000 grams of an aqueous solution containing 45% TMP (starting acid wash color 9–10 Gardner units, phthalic anhydride color 200 APHA units) was mixed with 2300 grams of methyl tertiary butyl ether (MTBE) solvent in a separatory funnel at ambient temperature, about 25° C. The mixture was shaken vigorously for 5 minutes and the phases were allowed to settle and the aqueous phase separated from the organic phase by decantation. After removing the water, the recovered TMP (82% recovery efficiency based on the starting amount of TMP) had an acid wash color of 3.5 Gardner units and a phthalic anhydride color of 60 APHA units. Multiple repetitions of the procedure were used to remove additional color bodies.

TABLE III

| STAGE | GARDNER UNITS | APHA | TMP RECOVERY |
| --- | --- | --- | --- |
| 1 | 3.5 | 60 | 82% |
| 2 | 2.0 | 40 | 78% |
| 3 | 1.4 | 30 | 72% |
| 4 | 0.9 | 30 | 68% |

EXAMPLE 4

Using the perforated plate extractor as described in Example 1, the counter-current liquid-liquid extraction was carried out at 35° C., using MTBE as a solvent. In this example the MTBE solvent was the dispersed phase and water was the continuous phase. The MTBE feed rate was 37 g/min and the feed rate of the aqueous 60% TMP was 16 g/min. The extraction was continued for 6 hours. The TMP product recovered from the raffinate and dried to about 5% water, gave an average acid wash color of 1.9 Gardner units. The average phthalic anhydride color was 50 APHA units. The average recovery of improved color TMP was 89%.

EXAMPLE 5

The procedure was carried out using the same conditions as described in Example 4, except that a 45% aqueous TMP solution was used. The average color of the recovered TMP product was 0.9 Gardner units. The average phthalic anhydride color was 30 APHA units The average recovery of TMP product was 89%.

The following example illustrates the level of reacted color of TMP typically produced by commercial processes and operations known in the art. Both crude TMP before final distillation and finished purified TMP product after distillation are examined and show relatively high levels of reacted color. As described previously, this level of reacted color in TMP is undesirable in certain color-sensitive end uses, e.g. in radiation-cured coatings.

COMPARATIVE EXAMPLE 1

A TMP was made according to U.S. Pat. No. 3,183,274 (Example 1) by the reaction of n-butyraldehyde, formaldehyde, and sodium hydroxide. After following the recommended reaction procedure, the reaction mixture was neutralized with formic acid to a pH of 6–7. The excess formaldehyde was removed by distillation leaving an aqueous solution of TMP, organic by-products produced in the reaction, and sodium formate. The TMP was quantitatively isolated from the aqueous solution of sodium formate together with most of the other organic compounds present by extraction with ethyl acetate as a solvent. The ethyl acetate was then removed from the extract by flashing leaving a crude TMP product. This crude TMP had an acid wash color of 16–18 Gardner units and phthalic anhydride color of 700 units. The crude TMP was then distilled under vacuum, as is done commercially to purify TMP, to yield a finished purified TMP product having an acid wash color of 9–10 Gardner units and a phthalic anhydride color of 200 APHA units.

We claim:

1. In a process for the recovery of trimethylolpropane (TMP) from the aqueous base solution in which it is prepared comprising neutralizing the base, extracting the TMP into an organic solvent phase, and separating the TMP from the organic solvent the improvement which comprises further extracting an aqueous solution of the TMP with an ester or ether selected from the group comprising ethyl tert. butyl ether, diethyl ether, dipropyl ether, methyl tert. butyl ether, diglyme, esters containing from 2 to about 9 carbon atoms, methyl formate, methyl acetate, ethyl formate, ethyl acetate, butyl propionate, ethylene glycol, propylene glycol, $C_1$–$C_4$ acids, or mixtures thereof to obtain an aqueous solution of TMP which is purified in known manner to obtain TMP in greater than about 60% yield and having improved color as characterized by an acid wash color of 3 Gardner units or less and phthalic anhydride color of 100 or less APHA units.

2. The process of claim 1 wherein the ether or ester is diethyl ether, methyl tert. butyl ether, dipropyl ether, ethyl tert. butyl ether, diglyme (diethylene glycol dimethyl ether), esters containing from 2 to about 9 carbon atoms, and esters of ethylene glycol or propylene glycol with $C_1$–$C_4$ acids, or mixtures of said esters and ethers.

3. The process of claim 1 wherein the second extraction is carried out as a continuous liquid-liquid extraction.

4. The process of claim 1 wherein the second extraction is carried out as a batch liquid-liquid extraction.

5. The process of claim 1 wherein the ester or ether is recycled ester or ether.

6. The process of claim 1 wherein the ester or ether is fresh ester or ether.

7. The process of claim 1 wherein the obtained TMP has an acid wash color of 2 or less Gardner units and a phthalic anhydride color of 70 or less APHA.

8. The process of claim 7 wherein the obtained TMP has a color of 1 or less Gardner units and a phthalic anhydride color of 50 or less APHA.

9. The process of claim 1 which is carried out at from about 0° C. to about 100° C. using an ester or ether to feed weight ratio of from about 5:1 to about 1:2 and a feed of from about 30% to about 80% TMP in water.

10. The process of claim 9 which is carded out at from about 15° C. to about 40° C., using an ester or ether to feed weight ratio of about 4:1 to 2:1 and a feed of from about 45% to about 65% TMP in water.

11. The process of claim 10 wherein the ester or ether for the second extraction is diethyl ether, methyl tert. butyl ether, methyl formate, ethyl acetate, or mixture thereof.

12. The process of claim 11 wherein the ester or ether for the second extraction is methyl tert. butyl ether.

13. The process of claim 11 wherein the ester or ether for the second extraction is diethyl ether.

14. The process of claim 11 wherein the ester or ether for the second extraction is methyl formate.

\* \* \* \* \*